United States Patent [19]

Southern et al.

[11] Patent Number: 5,436,327
[45] Date of Patent: Jul. 25, 1995

[54] SUPPORT-BOUND OLIGONUCLEOTIDES

[75] Inventors: Edwin M. Southern; Uwe Maskos, both of Oxford, Great Britain

[73] Assignee: Isis Innovation Limited, Oxford, England

[21] Appl. No.: 669,412

[22] PCT Filed: Sep. 21, 1989

[86] PCT No.: PCT/GB89/01114
§ 371 Date: Mar. 20, 1991
§ 102(e) Date: Mar. 20, 1991

[87] PCT Pub. No.: WO90/03382
PCT Pub. Date: Apr. 5, 1990

[30] Foreign Application Priority Data

Sep. 21, 1988 [GB] United Kingdom ............... 8822228

[51] Int. Cl.⁶ ............................................. C07H 21/04
[52] U.S. Cl. .............................. 536/25.34; 536/25.3; 536/25.31; 536/24.3
[58] Field of Search ................ 536/27, 25.34, 25.31, 536/25.3, 24.3; 435/6; 935/19, 88

[56] References Cited

U.S. PATENT DOCUMENTS

| | | | |
|---|---|---|---|
| 4,458,066 | 7/1984 | Caruthers et al. | 536/25.34 |
| 4,591,614 | 5/1986 | Miller et al. | 536/27 |
| 4,668,777 | 5/1987 | Caruthers et al. | 536/27 |

OTHER PUBLICATIONS

Pierce Handbook and General Catalog. Pierce Chemical Co. 1979-1980, p. 361.
Sigma Chemical Co. Handbook 1989, p. 142.
Pon et al. BioTechniques 6(8):768-775 (1988).
Crea et al. Nucl. Acids Res. 8(10):2331-2348 (1980).
Gilham, P. T. J.A.C.S. 86:4982-4985 (1964).
Froehler et al. Nucl. Acids Res. 14(13):5399-5407.

Primary Examiner—Douglas W. Robinson
Assistant Examiner—Gary L. Kunz
Attorney, Agent, or Firm—Wenderoth, Lind & Ponack

[57] ABSTRACT

A method for synthesizing oligonucleotides by solid-phase methodology wherein the linkage between the oligonucleotide and the solid phase support is a nonlabile phosphodiester. The spacer arm between the support and the phosphodiester is a hydrophilic group. The product of this method is an immobilized oligonucleotide which can be used in solid phase hybridization assays.

8 Claims, No Drawings

SUPPORT-BOUND OLIGONUCLEOTIDES

There are several potential applications for oligonucleotides bound to solid supports. They could be used to test for the presence of mutations in complex DNAs— for example for disease loci in Humans. They could be used to select specific nucleic acids from the complex mixtures; for example specific mRNAs from a whole cell population. They will be useful in the invention described in International Application PCT/GB89/00460 filed 2 May 1989.

Several papers describe methods for attaching nucleic acids to solid matrices (1-6). These methods suffer from two problems: they require complex and often inefficient steps; the nucleotide is linked through the bases as well as the ends. Linkage through the bases interferes with subsequent use of the bound polynucleotide in hybridization reactions.

Methods for synthesizing oligonucleotides on solid supports are well established (7-14). The linkage between the oligonucleotide and the support is labile to the the final reagent used to remove blocking groups in the bases, and so this step in the process also removes the oligonucleotide from the solid support. Oligonucleotides would remain tethered to the support of a stable link were used. Sproat and Brown (1985) have shown that a urethane link is more stable than the usual succinate link, however, it requires a complex synthesis, and is not completely stable to the final deprotection step.

Crea and Horn (1980) used a ribonucleotide, linked through the 5'-hydroxyl group to cellulose, to initiate oligonucleotide synthesis. The link between the first and second residues of the resulting chain is labile to the final deprotection step.

Arnold and Berg (1985) describe a polymeric support with a covalently bonded primer for oligonucleotide synthesis, wherein the primer is cleaved by selective oxidation without oxidizing other bonds of the oligonucleotide.

It is an object of this invention to provide a new link which is easy to synthesize and completely stable to standard deprotection steps.

In one aspect the invention provides a method of making a derivatized support suitable for oligonucleotide synthesis, which method comprises attaching a nucleoside reagent to a support carrying hydroxy groups by a covalent phosphodiester link which is stable to conditions used for removing protective groups from oligonucleotide chains, characterized in that the hydroxyl groups are aliphatic hydroxyl groups in which the aliphatic moiety is $-(C_nH_{2n})-$ where n is at least 3 or alkoxy or poly(alkoxy).

In another aspect the invention provides a method of preparing an oligonucleotide bound to a support by
a) attaching a nucleoside reagent to a support,
b) synthesizing on the supported nucleoside an oligonucleotide chain including protecting groups, and
c) removing the protecting groups from the oligonucleotide chain,
wherein the support carries hydroxyl groups, whereby in step a) the nucleoside becomes attached to the support by a covalent phosphodiester link which is stable to the conditions used in step c), characterized in that the hydroxyl groups are aliphatic hydroxyl groups in which the aliphatic moiety is $-(C_nH_{2n})-$ where n is at least 3 or alkoxy or poly(alkoxy).

In a further aspect the invention provides a derivatized support suitable for oligonucleotide synthesis comprising a nucleoside linked to a support by means of a covalent phosphodiester link of the structure —O—PY—O—, where Y is a protected or unprotected oxygen atom characterized in that the link to the support is through an aliphatic moiety which is $-(C_nH_{2n})-$ where n is at least 3 or alkoxy or poly(alkoxy).

In yet another aspect the invention provides a support-bound oligonucleotide wherein the oligonucleotide is bound to the support through a terminal phosphate group by a covalent phosphodiester link, characterized in that the link has the structure —O—PO$_2$—O—R— where R is an aliphatic moiety which is $-(C_nH_{2n})-$ where n is at least 3 or alkoxy or poly(alkoxy).

The nature of the support is not critical to the invention. It may be massive or particulate and may for example be of derivatized silica gel or Kieselguhr-polydimethyl-acrylamide, or controlled-pore glass, or a plain glass surface. What is essential is that it carry aliphatic hydroxyl groups, and these in a form which are accessible for reaction with a nucleoside reagent. These hydroxyl groups may form part of hydroxy alkyl groups, such as may be formed by derivatizing controlled-pore glass or other support with a long chain alkyl alcohol. Alternatively, the support may be derivatized with a long chain alkylamine, and the amine groups converted to hydroxyl groups in situ. Alternatively, the hydroxyl groups may be part of a polymeric structure, which either constitutes the solid support or is derivatized onto a solid support.

The nature of the nucleoside reagent is not critical to the invention. Reagents commonly used in oligonucleotide synthesis may be used here. Preferably, the reagent is a phosphoramidite (7 and 8). The reagents and the product formed are indicated in the following reaction scheme.

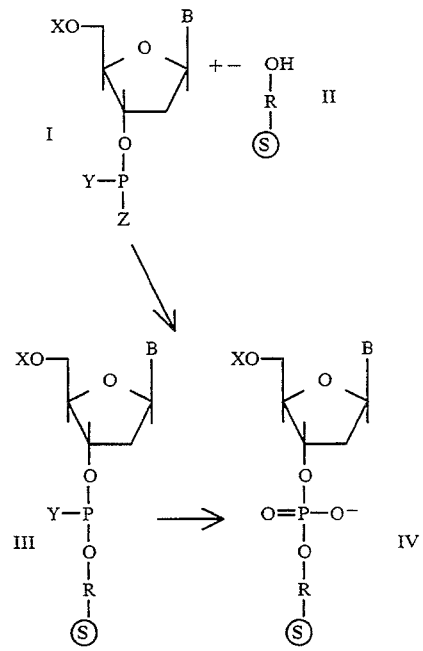

In this scheme, I represents the nucleoside 3'-phosphite reagent, II represents the derivatized support, III represents the covalent link initially formed by reaction between the two, and IV represents the final product.

B designates the base appropriate to the nucleoside concerned.

X may be a blocking group, such as a dimethoxytrityl group, whose nature is not critical to the invention; or may (particularly in IV) represent an oligonucleotide chain.

Y is a protected oxygen atom, generally an alkoxy group such a methoxy or beta-cyanoethoxy.

Z may be a di-(C1 to C4 alkyl)amine, or alternatively Cl or tetrazolyl.

R is aliphatic and may be an alkyl group.

S represents the solid support.

Alternatively, the nucleoside 3'- reagent may be a phosphonate or hydrogen phosphonate (12). The reagent and the product formed are indicated in the following reaction scheme.

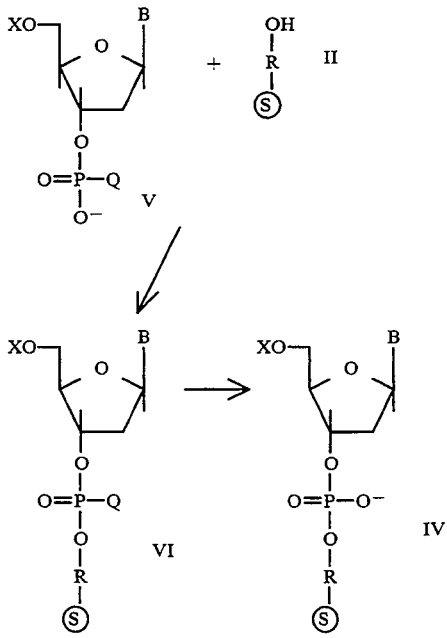

In this scheme, V represents the nucleoside phosphonate or hydrogen phosphonate reagent, II represents the derivatized support, VI represents the covalent link initially formed between the two, and IV represents the final product.

B, X, R and S are as defined above

Q is either hydrogen or an organic group that plays no part in the attachment and synthesis steps of the invention.

Alternatively again, the nucleoside 3'- reagent may be a phosphonamidite having the stucture VII where A is alkyl and B, X and Z are as defined as above. In a preferred example, A is methyl and Z is diisopropylamine

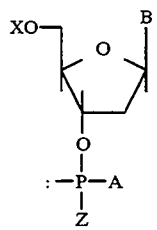

Automatic oligonucleotide synthesizers are commercially available. In prior techniques, it has been necessary to put into the synthesizer a solid support which has been pre-derivatized with the first nucleotide of the proposed oligonucleotide chain. This invention makes it possible to put into the synthesizer a solid support which carries aliphatic hydroxyl groups (e.g. hydroxyalkyl groups). The nucleoside 3'- reagent is then attached to the support in the synthesizer as the first nucleotide of the proposed oligonucleotide chain.

In the above reaction schemes, conversion of III to IV or of VI to IV involves an oxidation step. This may be effected using e.g. iodine or sulphur under standard conditions, either before or more usually after oligonucleotide synthesis.

Nucleoside 3'- reagents are more developed than are nucleoside 5'- reagents for solid state oligonucleotide synthesis. Nevertheless, nucleoside 5'-reagents are expected to form covalent 5'-phosphodiester links with solid supports carrying aliphatic hydroxyl (e.g. hydroxyalkyl) groups, and to serve as a basis for solid state oligonucleotide synthesis, in exactly the same way as their 3'- counterparts. This invention envisages the use of nucleoside 5'- reagents as alternatives to nucleoside 3'- reagents.

The next step of the method involves synthesizing on the supported nucleoside an oligonucleotide chain. Techniques for doing this are well known, and indeed automatic microprocessor-controlled machines are available to do the job. These techniques invariably involve the provision of protective groups to avoid unwanted side reactions, and a final step in the synthesis of any oligonucleotide involves removal of protecting groups. It is this step that has previously resulted in solubilization of the oligonucleotide. This step may typically involve removal of the methyl group from the phosphotriester groups e.g. by using thiophenoxide; removal of protecting groups from N atoms of the nucleotide bases, e.g. by means of ammonia at elevated temperature; and removal of a protective group from the 5'-position of the last nucleotide to have been added to the oligonucleotide chain, e.g. by means of dichloro acetic acid. The described covalent link between the initial nucleoside and the support is stable to these and other conventional deprotection steps.

The following examples illustrate the invention.

EXAMPLE 1

Ballotini glass beads (20 g, 90–130 μm diam., Jencons), were suspended in a mixture of xylene (40 ml), glycidoxypropyltrimethoxysilane, and a trace of diisopropylethylamine at 90° C. overnight with stirring, then washed thoroughly with methanol, ether and air-dried. These derivatized beads (6 g) were heated with stirring in hexaethyleneglycol containing a catalytic amount of concentrated sulphuric acid, overnight in an atmosphere of argon, at 80° C., to yield alkyl hydroxyl derivatized beads. After washing with methanol and ether, the beads were dried under vacuum and stored under argon at −20° C.

A small amount of the hydroxyalkyl derivatized beads was put into the reaction vessel of an automatic oligonucleotide synthesizer (Applied Biosystems), programmed to synthesize the sequence of the left cohesive end of bacteriophage lambda. The first nucleotide was a 3′-phosphoramidite (I) in which Y was beta-cyanoethoxy and Z was di-isopropylamine. This became covalently attached to the derivatized beads.

Each step in the synthesis can be monitored by measuring the amounts of trityl group removed, in the spectrophotometer. By this test, the stepwise yield was 96–99%. Thus both yield and purity were high, and we calculate that the 140 mg of beads holds more than 4 nmol of the oligonucleotide.

The product was deprotected by the standard treatment with hot ammonia and washed thoroughly with distilled water. Is was then used in a hybridization with the complementary oligonucleotide cosL which had been labelled at the 5′ end with 32P.

To 1 mg of beads derivatized with the left end of phage lambda (cosL) was added the complementary oligonucleotide, radioactively labelled (13,000 cpm $^{32}$P in 20 μl, 100 mM NaCl, 1 mM EDTA). The mixture was incubated for 2 hours at 30° C., the radioactive solution removed and the beads washed thoroughly with ice cold buffer. The oligonucleotide which remained attached to the beads (ca. 3,000 cpm, 23%) could be quantitatively removed by elution with distilled water.

A control "hybridization" under identical conditions, with a non-complementary oligonucleotide showed 0.02% of non-specific binding to the beads.

These experiments show that the synthesis is straightforward and that the beads can be used successfully in hybridization tests.

The glass beads are ideal for packing columns to provide an affinity matrix with many desirable properties.

The following Table 1 summarises physical parameters of beads derivatized by the general technique described in Example 1.

TABLE 1

| Properties of derivatized ballotini beads | | |
| --- | --- | --- |
| Bead size (microns) | 90–130 | 3–6 |
| surface area per bead (mm$^2$) | 0.045 | 0.00011 |
| volume per bead (mm$^3$) | 9 × 10$^{-4}$ | 1.1 × 10$^{-7}$ |
| density (g/cm$^3$) | 2.5 | 2.5 |
| mass per bead (mg) | 0.0023 | 2.8 × 10$^{-7}$ |
| number of beads per (mg) | 435 | 3.5 × 10$^6$ |
| surface area per mg (mm$^2$) | 19.5 | 385 |
| oligonucleotide loading per mg (pmol) | ~80 | ~80 |
| oligonucleotide loading per bead (fmol) | 184 | 0.02 |
| values calculated for radius (microns) | 60 | 3 |

EXAMPLE 2

Two glass plates were clamped together with a narrow gap between them. Derivatization was effected by means of the same reagents, which were injected into the narrow gap, and under the same conditions as Example 1.

Oligonucleotide synthesis was performed by hand under standard conditions using the derivatized glass plate as a solid support. The first nucleotide was 3′-hydrogen phosphate, used in the form of the triethylammonium salt. The yield and purity of both the first and subsequent steps of the oligonucleotide synthesis were high.

The following Examples demonstrate several ways of hybridizing labelled DNA fragments and oligonucleotides to the derivatized beads.

EXAMPLE 3

Hybridization to glass beads attached to sticks.

A plastic stick 2 cm long was dipped into molten polypropylene and then brought into contact with a pile of derivatized glass beads and allowed to cool. Approximately 100–200 beads adhered to the stick. This method of holding the beads greatly facilitates hybridization as will be shown in a number of typical experiments:

A stick with approximately 100 glass beads derivatised with the sequence 3′ AGG TCG CCG CCC 5′ was dipped into 30 ul of a solution containing 0.1M NaCl and 80 fmol of the complementary oligonucleotide, labelled at the 5′ end to an activity of 30,000 cpm.

After 30 min at 30° C. the stick was removed from the tube, rinsed and the bound material eluted by dipping the stick into 0.1M NaCl at 50° C. The amount of oligonucleotide hybridized was then determined by scintillation counting.

Typically 4% of the input olignucleotide could be picked up this way; 0.1% were bound nonspecifically and could not be removed. Thus the binding capacity of a single bead is approximately 0.03 fmol oligonucleotide.

Larger proportions of the initial oligonucleotide could be picked up by decreasing the temperature and increasing the length of the hybridization. Thus in a similar experiment 5.3% was hybridized at 30° C. after 55 minutes with 0.05% bound nonspecifically, and 13% after 16 hours at 30° C. with 0.2% binding nonspecifically.

As a control, noncomplementary oligonucleotide 5′ GGG CGG CGA CCT 3′ showed only 0.2% binding after 14 hours.

In summary, experiments with derivatized glass beads attached to plastic sticks have proved to be very easy and shown the high specificity of hybridization to the beads.

EXAMPLE 4

Batch hybridization.

The amount of radioactive material hybridizing to the be ads could be increased further, and the nonspecific binding decreased by carrying out hybridization with beads typically 1 mg in 0.5 ml centrifuge tubes. After hybridization the tubes were spun, the supernatant removed and the beads washed. Washing at a temperature higher than $T_m$ resulted in complete melting of the hybrids so that the bound material could be measured by Cerenkov counting. In this way we determined the dependence of rate of hybridization and elution on salt concentration and temperature as follows:

To each of 5 tubes as added an approximately equal number of beads and complementary oligonucleotide (30,000 cpm) in 50 μl of 0.1M NaCl. Hybridization was carried out at 30° C. overnight to maximize the amount of hybrid. The solution was removed and the beads washed twice with ice-cold 0.1M NaCl. Elution was for increasingly longer times at a different temperature for each tube. After each interval the supernatant was removed, the beads were washed twice with ice-cold NaCl solution (100 μl 0.1M), and eluted with pre-warmed NaCl solution (100 μl 0.1M).

Table 2 details the percentage of bound oligonucleotide eluted in the course of time. There is a clear dependence of elution rate on temperature. For example, three times as much material eluted at 65° C. than at 30° C., within 5 minutes. Not suprisingly, even at 30° C. which is well below $T_m$, there is a non-negligible rate.

In an other experiment the concentration of input oligonucleotide was varied 50 fold. Hybridization for 2 hours at 30° C. in 0.1M NaCl, 1 mM EDTA in 1.5 ml centrifuge tubes was followed by removal of the supernatant, three washes with 0.1M NaCl at 0° C. and the amount of radioactivity associated with the beads determined by Cerenkov counting. There is an almost linear relationship between concentration and amount of hybrid (i.e. rate of hybridization, Table 3), which suggests that the hybridization is a pseudo first order reaction.

The highest concentration of oligonucleotide was 160 fmol (corresponding to 13,000 cmp) in 20 μl. Only 0.03% bound nonspecifically and could not be eluted.

Furthermore, only 0.02% non-complementary oligonucleotide bound to the beads in a similar experiment (12 out of 65,000 cpm), a further indication that this method of isolating DNA fragments is very specific and clean.

TABLE 2

| Elution time temperature | Effect of temperature on elution rate | | | | | |
|---|---|---|---|---|---|---|
| | 5' | 20' | 50' | 110' | 330' | |
| | % eluted | | | | | % remaining |
| 30° C. | 23 | 38 | 54 | 71 | 85 | 0 |
| 36° C. | 34 | 61 | 78 | 90 | 96 | 3 |
| 44° C. | 42 | 54 | 67 | 87 | 97 | 2 |
| 65° C. | 74 | 89 | 96 | 98 | 98 | 1.4 |

TABLE 3

| Effect of oligonucleotide concentration on hybridization rate | | | | | |
|---|---|---|---|---|---|
| Relative concentration | 50 | 20 | 10 | 2 | 1 |
| % hybridized | 23 | 14 | 5.5 | 0.8 | 0.6 |
| relative rate | 38 | 23 | 9 | 1.5 | 1 |

EXAMPLE 5

Isolation of longer DNA fragments:

The isolation of longer DNA fragments was demonstrated in the following experiments: Total λ DNA (5 μg in 35 μl restriction enzyme buffer) was digested with 15 units of the restriction endonuclease Hinf 1 and the resulting 143 restriction fragments dephosphorylated with calf intestinal phosphatase (1 unit). After one hour at 37° C. 4 μl of EGTA was added, the mixture incubated for another 45 minutes at 65° C., phenol extracted and ethanol precipitated.

The mixture was dissolved in 50 μl kinase-labelling buffer (8 μl 10×PNK buffer, 1 μl 0.1M DTT, 4 μl PNK enzyme, 30 μl distilled water, 15 μCi-$^{32}$P.ATP), incubated for one hour at 37° C., made up to 100 μl and spun down a Sephadex G25 column to remove non-incorporated nucleotides.

An aliquot of the ballotini glass beads (100 μm, Jencons) was derivatised with the sequence of the right cohesive end of bacteriophage lamba, viz. 3'- CCC GCC GCT GGA 5', deprotected in ammonia, washed, and a small amount put at the bottom of a U-shaped capillary. This bottom part was kept at 40° C. in a controllable temperature block, the upper left and right arms of the capillary were kept at 67° C. by jacketing them with a plastic syringe and pumping hot water through it. The hybridization solution was added (75 μl 0.1M NaCl containing 10 pmol 5' ends, 33 fmol left λ cohesive ends complementary to the oligonucleotide on the beads, total radioactivity ca. 700,000 cpm).

A pump was attached to one arm of the capillary and the hybridizing solution cycled back and forth between the parts of the capillary that were kept at 40° C. and 67° C. respectively. Hybridization of the left end to the beads would occur at 40° C., and at 67° C. the two sticky lambda ends that reannealed in solution would be denatured.

After 4 hours the hybridization solution was removed, the beads washed extensively, then eluted in hot TE. An aliquot of the solution was loaded onto a 5% polyacrylamide gel. Autoradiography revealed only one band of the correct size in the washes and elution lanes. Altogther 1000 cpm (ca. 1.5 fmol) of the left end were bound by the beads which corresponded to 5% of the theoretical amount.

In summary, this experiment demonstrates the highly specific isolation of a long DNA fragment from a complex mixture.

EXAMPLE 6

Column Chromatography.

Another easy and convenient way to isolate oligonucleotide and to test the hybridization behaviour of the novel support is by column chromatography.

A glass capillary (diameter 1.0 mm) was drawn out at one end so as to yield a very narrow pointed opening. This was then plugged by filling in crushed glass particles from the other end and sintering them in the flame of a Bunsen burner so that they adhered to the glass. The inside of the capillary was silanised by passing through a solution of dichlorodimethyl-silane in trichloroethane and washing with ethanol. Approximately 40 mg of the glass beads were layered on the glass frit and the top of the column connected to a syringe that could be driven by an infusion pump. In this way radioactive hybridization solution and washing solutions could be applied to the column at different rates, typically in the range of 3–10 μl/min.

In a typical experiment, 0.2 pmol of labelled oligonucleotide (34,000 cpm) in 1 ml of a solution of 0.1M NaCl, 0.1% SDS in TE pH 7.5 was applied to the column at a rate of 3 μl/min. The jacketed column was kept at 35° C. 90 μl fractions were collected in microcentrifuge tubes and the amount of radioactivity determined by Cerenkov counting. A 0.1M NaCl washing solution was applied in the same way and collected. Raising the temperature in the jacket allowed us to recover the oligonucleotide.

Thus it was determined that 70% of the oligonucleotide bound to the glass beads and could be eluted at a higher temperature with only 0.1% of the material remaining on the support.

A control experiment with non-complementary oligonucleotide (mismatch at position 7) showed a remaining 400 cpm out of 80,000 applied after washing at 35° C. At 40° C. only 140 cpm=0.2% remained.

The percentage of accessible oligonucleotide on the support was determined. 0.13 pmol kinase-labelled and 5 pmol unlabelled oligonucleotide were applied to 40 mg beads. 10% of the material (ca. 500 fmol) hybridized to the support that contained a total of ca.3 nmol oligonucleotide, measured from the detritylation during synthesis.

From this result we calculate that one in 6000 oligonucleotides on the support hybridized under conditions used (35° C., low salt) where negligible binding of mismatched oligonucleotides occurs. The melting was very sharp again, with most of the oligonucleotides eluted in two 90 μl fractions at 48° C.

These experiments suggest that the derivatized beads will be useful in the chromatographic separation of nucleic acids.

REFERENCES

1. Langdale J. A. and Malcolm A. D. (1985) A rapid method of gene detection using DNA bound to Sephacryl. Gene 1985, 36(3), 201–210.
2. Seed, B (1982) Diazotizable anylamine cellulose paper for the coupling and hybridization of nucleic acids. Nucl. Acids Res. 10, 1799–1810.
3. Allfrey and Inoue (1978) Affinity chromatography of DNA-binding proteins on DNA covalently attached to solid supports. Methods Cell Biol. 17, 253–270.
4. Banemann, H.; Westhoff, P. and Herrmann G. (1982) Immobilisation of Denatured DNA to Macroporous Supports: 1 Efficiency of different coupling procedures. Nucl. Acids Res. 10, 7163–7180.
5. Astell C. R. and Smith M. (1972) Synthesis and Properties of Oligonucleotide-Cellulose Columns. Biochemistry 11, 4114–4120.
6. Gilham P. T., Biochemistry, 7, No 8, 1968, 2809–13.
7. Matteucci M. D. and Caruthers M. H. J. Am. Chem. Soc. 1981, 103, 3185–3191.
8. Beaucage S. L. and Caruthers M. H. Tetrahedron Letters, Vol 22, No.20, pp 1859–1862, 1981.
9. Adams S. P. et al, J.Am. Chem. Soc. 1983, 105, 661–663
10. Sproat D. S. and Brown D. M. Nucleic Acids Research, Vol 13, No.8, 1985, 2979–2987.
11. Crea R. and Horn T., Nucleic Acids Research, 8, No 10, 1980, 2331–48.
12. Andrus A. et al., Tetrahedron Letters, Vol 29, No. 8, pp 861–4, 1988.
13. Applied Biosystems User Bulletin, Issue No. 43, Oct. 1, 1987, "Methyl phosphonamidite reagents and the synthesis and purification of methyl phosphonate analogs of DNA".
14. Miller P. S. et al., Nucleic Acids Research, 11, pages 6225–6242, 1983.
15. Arnold L. J. and Berg R. P., Molecular Biosystems Inc. PCT Application WO 85/01051.

We claim:

1. In a method of preparing an oligonucleotide bound to a support by
    a) attaching to a support a 2'-deoxynucleoside reagent selected from the group consisting of nucleoside 3' reagents and nucleoside 5' reagents which reagent is selected from the group consisting of phosphite, phosphonate, hydrogen phosphonate, phosphonamidite, phosphoramidite and methylphosphonamidite reagents,
    b) synthesizing on the supported nucleoside an oligonucleotide chain including protecting groups, and
    c) removing the protecting groups from the oligonucleotide chain,
    wherein the support carries hydroxyl groups, whereby in step a) the nucleoside becomes attached to the support by a covalent phosphodiester link which is stable to the conditions used in step c),
    the improvement wherein the groups carried by the support have the formula —ROH, where R is selected from the group consisting of alkoxy, poly(alkoxy) and —($C_nH_{2n}$)— wherein n is at least 3.

2. The method as claimed in claim 1, wherein the support is of porous glass or glass beads.

3. The method as claimed in claim 1, wherein the nucleoside reagent is a nucleoside 3'-phosphoramidite.

4. The method as claimed in claim 1, wherein the nucleoside reagent is a nucleoside 3'-phosphite.

5. The method as claimed in claim 1, wherein the nucleoside reagent is a nucleoside 3'-phosphonate or 3'-hydrogen phosphonate.

6. The method as claimed in claim 1, wherein the nucleoside reagent is a nucleoside 3'-methylphosphonamidite.

7. The method as claimed in claim 1 wherein step c) involves removing protecting groups from phosphotriester groups and from N atoms of the nucleotide bases and from the 5'-position on the last nucleotide of the chain.

8. The method of claim 1, wherein the covalent phosphodiester link is —O—PY—O—R—, where Y is a protected or unprotected oxygen atom.

* * * * *